US00PP35200P2

(12) United States Plant Patent
Snijder

(10) Patent No.: US PP35,200 P2
(45) Date of Patent: May 30, 2023

(54) ***PELARGONIUM* PLANT NAMED 'PEQZ0093'**

(50) Latin Name: ***Pelargonium* interspecific**
Varietal Denomination: PEQZ0093

(71) Applicant: SYNGENTA CROP PROTECTION AG, Basel (CH)

(72) Inventor: Ronald Christiaan Snijder, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/939,235

(22) Filed: Sep. 7, 2022

(51) Int. Cl.
*A01H 5/02* (2018.01)
*A01H 6/42* (2018.01)

(52) U.S. Cl.
USPC ..... Plt./329

(58) Field of Classification Search
USPC ..... Plt./329, 324, 325

CPC ... A01H 5/02; A01H 5/00; A01H 6/42; A01H 6/425

See application file for complete search history.

(56) References Cited

U.S. PATENT DOCUMENTS

PP29,948 P3 * 12/2018 Snijder ..... A01H 6/42 Plt./324

OTHER PUBLICATIONS

Canadian Food Inspection Agency 2023, retrieved on Jan. 25, 2023 at https://inspection.canada.ca/english/plaveg/pbrpov/cropreport/pel/app00012830e.shtml, 2 pp. (Year: 2023).*

* cited by examiner

*Primary Examiner* — June Hwu
(74) *Attorney, Agent, or Firm* — Dale Skalla

(57) ABSTRACT

A new *Pelargonium* plant named 'PEQZ0093' particularly distinguished by large red purple colored inflorescences with large semi-double florets, held above dark green zoned foliage, on a vigorous upright plant.

1 Drawing Sheet

Latin name of the genus and species of the plant claimed: *Pelargonium* interspecific.

Varietal denomination: 'PEQZ0093'.

BACKGROUND OF THE NEW PLANT

The present invention comprises a new *Pelargonium*, botanically known as *Pelargonium* interspecific, and hereinafter referred to by the variety name 'PEQZ0093'.

'PEQZ0093' is a product of a planned breeding program. The new cultivar 'PEQZ0093' has large red purple colored inflorescences with large semi-double florets, held above dark green zoned foliage, on a vigorous upright plant.

'PEQZ0093' originates from a hybridization in a controlled breeding program made in July 2015, in a greenhouse in Enkhuizen, The Netherlands. The female parent was an unpatented plant of *P.* x *hortorum* parentage identified as 'PEZ-AZ3272-01V' with red florets, when compared to 'PEQZ0093'.

The male parent of 'PEQZ0093' was an unpatented, proprietary plant of *P.* x interspecific parentage, identified as '10301-1V' with lighter green foliage and purple florets when compared to 'PEQZ0093'. The resultant seed was sown in December 2015.

'PEQZ0093' was selected as one flowering plant within the progeny of the stated cross in May 2016 in a greenhouse in Enkhuizen.

The first act of asexual reproduction of 'PEQZ0093' was accomplished when vegetative cuttings were propagated from the initial selection in June 2016 in a greenhouse in Enkhuizen, The Netherlands.

BRIEF SUMMARY OF INVENTION

Horticultural examination of plants grown from cuttings of the plant initiated in May 2016 in Enkhuizen, The Netherlands and continuing thereafter, has demonstrated that the combination of characteristics as herein disclosed for 'PEQZ0093' are firmly fixed and are retained through successive generations of asexual reproduction.

'PEQZ0093' has not been observed under all possible environmental conditions. The phenotype may vary significantly with variations in environment such as temperature, light intensity, and day length.

A Plant Breeder's Right for this cultivar was applied in Canada on Oct. 25, 2022, No. 22-11116. 'PEQZ0093' has not been made publicly available prior to the effective filing date of this application, notwithstanding any disclosure that may have been made less than one year prior to the effective filing date of this application by the inventor or another who obtained 'PEQZ0093' directly from the inventor. The following traits have been repeatedly observed and are determined to be the basic characteristics of the new variety. The combination of these characteristics distinguishes this *Pelargonium* as a new and distinct variety.

BRIEF DESCRIPTION OF THE PHOTOGRAPHS

The accompanying photographic drawings show typical flower and foliage characteristics of 'PEQZ0093' with colors being as true as possible with an illustration of this type.

Figure 1:
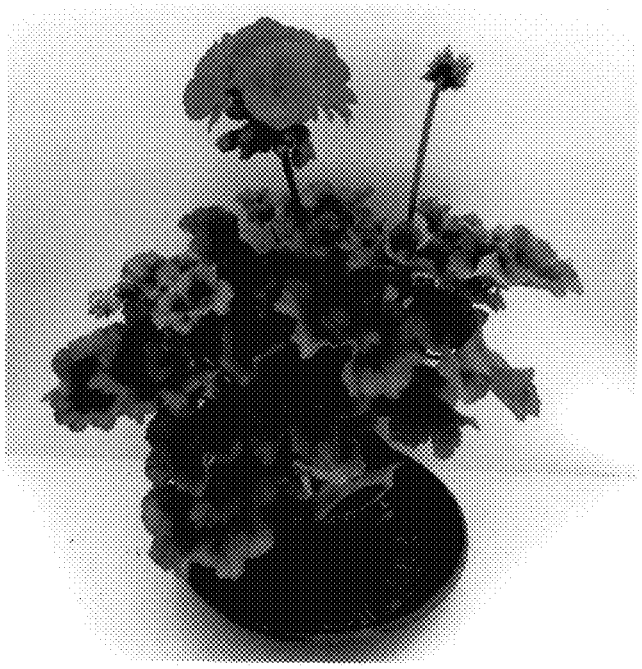
Figure 2:
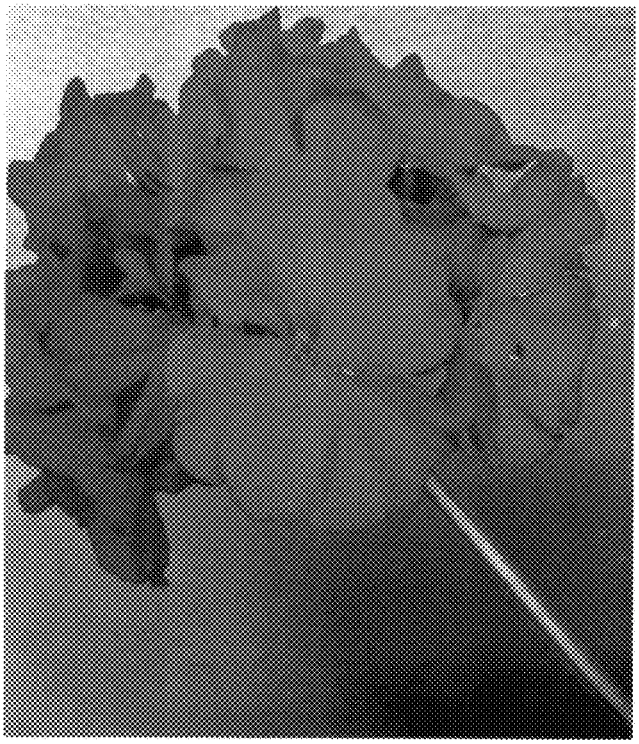

The photographic drawings show in FIG. 1, one flowering plant of the new variety and in FIG. 2, a close-up of an inflorescence.

DETAILED BOTANICAL DESCRIPTION

The plant descriptions and measurements were taken in Enkhuizen, The Netherlands in late June 2022 under natural light. Plants were approximately 22 weeks old and were grown in a 15 cm pot, in a greenhouse trial. The plant shown in the photograph was about 16 weeks old growing in a 12 cm pot in a greenhouse. The photographs were taken in April 2021.

Color references are made to The Royal Horticultural Society Colour Chart (R.H.S.) 2001.

TABLE 1

DIFFERENCES BETWEEN THE NEW VARIETY 'PEQZ0093' AND A MOST SIMILAR VARIETY

| | 'PEQZ0093' | 'PEQZ0096', U.S. application Ser. No. 17/939,430 |
|---|---|---|
| Color of pollen: | RHS 31A | RHS N 172A |
| Anther color: | RHS 180D | RHS 51B |
| Ovary color: | RHS 144A | RHS 187A |

Plant:

*Form, growth and habit.*—Upright growth habit.
*Plant height.*—29-32 cm.
*Plant height (inflorescence included).*—39-47 cm.
*Plant width.*—36-41 cm.

Roots:

*Number of days to initiate roots.*—15-18 days at about 22 degrees C.
*Number of days to produce a rooted cutting.*—21-23 days at 22 degrees C.
*Type.*—Fine, fibrous, free branching.
*Color.*—RHS N155B but whiter.

Foliage:

*Variegation.*—Absent.
*Immature leaf, color upper surface.*—Closest to RHS 137B.
*Immature leaf, lower surface.*—Closest to RHS 138B.
*Mature leaf, color upper surface.*—Closest to RHS 137A.
*Mature leaf, color lower surface.*—Closest to RHS 138B with some anthocyanin mottling, close to RHS 178B.
*Length.*—8-10 cm.
*Width.*—10-12 cm.
*Shape.*—Cordate.
*Base shape.*—Cordate.
*Sinus of mature leaf.*—Medium wide.
*Leaf base openness.*—Young leaves almost closed, more mature leaves open.
*Apex shape.*—Acute.
*Margin.*—Slightly dentate.
*Texture upper side.*—Hirsute.
*Texture lower side.*—Hirsute.
*Leaf zonation color.*—Between RHS N189A and RHS 187A.
*Leaf zone conspicuousness.*—Medium to strong.
*Undulation of leaf margin.*—Weak.
*Color of veins, upper surface.*—RHS 137A, largely indistinct.
*Color of veins, lower surface.*—RHS 144B, becoming indistinct.
*Pattern of veining.*—Palmate.
*Petiole color.*—RHS 143B, slightly mottled close to RHS 176B.
*Petiole length.*—5 cm.
*Diameter of petiole.*—0.2 cm.
*Texture.*—Pilose, hirsute, glandular hairs.

Stem:

*Quantity of branches.*—5-9.
*Color of stem.*—Close to RHS 143B.
*Anthocyanin coloration of stem.*—A strong anthocyanin coloration is visible under high solar radiation; RHS 187D when exposed.
*Length of stem.*—15-30 cm.
*Diameter.*—0.5 cm.
*Length of internodes.*—1-4 cm.
*Texture.*—Sparsely hirsute, pilose, glandular hairs.

Peduncle:

*Color of peduncle.*—At base RHS 144A with strong mottling RHS 176B at the base, fading to RHS 187A towards apex.
*Length of peduncle.*—16-26 cm.
*Peduncle diameter.*—0.3-0.5 cm.
*Texture.*—Hirsute, glandular hairs.
*Anthocyanin coloration of peduncle.*—A strong anthocyanin coloration is visible.

Pedicel:

*Color of pedicel.*—RHS 185A.
*Length of pedicel.*—2.5-3 cm.
*Diameter of pedicel.*—0.15-0.2 cm.
*Texture.*—Sparsely pilose, glandular hiars.
*Pedicel swelling.*—Swelling was not observed.

Bud (just before opening):

*Color.*—Between RHS 61A and RHS 61B.
*Length.*—1-1.2 cm.
*Width.*—0.6-0.7 cm.
*Shape.*—Elliptical.

Inflorescence:

*Type.*—Umbel; semi-spherical or nearly semi-spherical.
*Lastingness of individual flowers.*—7-9 days at 18° C. temperature.
*Number of inflorescences per plant.*—1-8, with 2-12 immature umbels in various stages.
*Average number of flower buds.*—20-30.
*Fragrance.*—None.
*Umbel diameter.*—12-15 cm.
*Umbel depth.*—8-10 cm.

Corolla:

*Form.*—Semi-double.
*Number of petals.*—6-9 with 0-2 petaloids.
*Diameter of flower.*—4.5-5 cm.
*Depth of flower.*—1.5-2 cm.
*Side view shape.*—Concave.
*Color upper petals, upper surface.*—Upper half between RHS N66A and RHS 61B; lower half RHS 44B and glistening, with veins RHS53A.
*Color upper petals, lower surface.*—Upper half close to RHS 53B, lower half RHS 44A with veins RHS 61B.
*Length of upper petals.*—2.2-2.5 cm.
*Width of upper petals.*—1.5-2 cm.
*Color lower petals, upper surface.*—Between RHS N66A and RHS 61B.
*Color lower petals, lower surface.*—RHS N66A, fading to RHS 67A at apex.
*Markings on upper petals.*—None.

*Markings on lower petals*.—None.
*Length of lower petals*.—2.2-2.5 cm.
*Width of lower petals*.—2.2-2.5 cm, petaloids variably smaller and with variable shape.
*Petal shape*.—Obovate to spathulate.
*Apex shape*.—Rounded.
*Margin*.—Entire.
*Base*.—Attenuate.
*Petal texture*.—Papillose on both surfaces.

Calyx:
*Number of sepals*.—5.
*Color of sepals*.—Apex RHS 144C, base RHS 187A.
*Length of sepals*.—1-1.4 cm.
*Width of sepals*.—0.2-0.4 cm.
*Sepal shape*.—Lanceolate to linear.
*Apex shape*.—Acute.
*Margins*.—Entire.
*Texture, upper surface*.—Glabrous.
*Lower surface*.—Glandular hairs, hirsute.
*Sepal flexing*.—Mostly unflexed sepals. The narrowest sepals might flex moderately.

Reproductive organs:

Gynoecium:
*Pistil length*.—0.9 cm
*Style color*.—RHS 59A. .
*Style length*.—0.4-0.5 cm.
*Stigma color*.—RHS 53A.
*Ovary color*.—RHS 144A.
*Ovary length*.—0.4-0.5 cm.
*Ovary diameter*.—0.2 cm.

Androecium:
*Number of stamens*.—6-9 with 1-5 staminoids.
*Color of filaments*.—RHS N155A fading towards RHS 68B.
*Length filaments*.—0.9-1 cm.
*Anther color*.—RHS 180D.
*Length of anthers*.—0.3 cm.
*Color of pollen*.—RHS 31A.
*Pollen amount*.—Ample.
*Fertility/seed set*.—Has not been determined to date.
*Disease/pest resistance*.—Has not been determined to date.

What is claimed is:

1. A new and distinct variety of *Pelargonium* plant named 'PEQZ0093' substantially as illustrated and described herein.

* * * * *